US008576535B2

(12) United States Patent
Sekoguchi

(10) Patent No.: US 8,576,535 B2
(45) Date of Patent: Nov. 5, 2013

(54) ION-GENERATING DEVICE AND ELECTRICAL APPARATUS

(75) Inventor: Yoshinori Sekoguchi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 319 days.

(21) Appl. No.: 13/001,813

(22) PCT Filed: Jun. 30, 2009

(86) PCT No.: PCT/JP2009/061910
§ 371 (c)(1),
(2), (4) Date: Dec. 29, 2010

(87) PCT Pub. No.: WO2010/004904
PCT Pub. Date: Jan. 14, 2010

(65) Prior Publication Data
US 2011/0102963 A1    May 5, 2011

(30) Foreign Application Priority Data

Jul. 7, 2008 (JP) ................................. 2008-177231

(51) Int. Cl.
*H01T 23/00* (2006.01)
(52) U.S. Cl.
USPC ...................................... 361/230; 250/423 F
(58) Field of Classification Search
USPC ........................................ 361/230; 250/423 F
See application file for complete search history.

(56) References Cited

U.S. PATENT DOCUMENTS

| 4,319,302 A * | 3/1982 | Moulden ....................... 361/213 |
| 4,729,057 A * | 3/1988 | Halleck ......................... 361/213 |
| 5,138,348 A * | 8/1992 | Hosaka et al. ................. 347/128 |
| 5,733,512 A * | 3/1998 | Tsai et al. ................. 422/186.15 |
| 2006/0024218 A1 | 2/2006 | Park et al. |
| 2009/0283692 A1 | 11/2009 | Sekoguchi |

FOREIGN PATENT DOCUMENTS

| JP | 8-255668 A | 10/1996 |
| JP | 9-35890 A | 2/1997 |
| JP | 9-289098 A | 11/1997 |
| JP | 10-199653 A | 7/1998 |
| JP | 2002-374670 A | 12/2002 |
| JP | 2004-432 A | 1/2004 |
| JP | 2006-40877 A | 2/2006 |
| JP | 2006-340740 A | 12/2006 |
| JP | 2008-16345 A | 1/2008 |
| JP | 2008-53000 A | 3/2008 |
| KR | 10-2006-0010233 A | 2/2006 |

* cited by examiner

*Primary Examiner* — Jared Fureman
*Assistant Examiner* — Scott Bauer
(74) *Attorney, Agent, or Firm* — Birch, Stewart, Kolasch & Birch, LLP

(57) ABSTRACT

An ion-generating device has a positive electrode pair and a negative electrode pair. The positive electrode pair and the negative electrode pair are disposed in a casing with a space interposed therebetween, such that an induction electrode in the positive electrode pair and an induction electrode in the negative electrode pair are separated from each other. It is thereby possible to obtain an ion-generating device and an electrical apparatus, capable of efficiently emitting both of positive ions and negative ions to an outside of the device, and easily achieving reduction in size and thickness.

30 Claims, 11 Drawing Sheets

ION-GENERATING DEVICE AND ELECTRICAL APPARATUS

TECHNICAL FIELD

The present invention relates to an ion-generating device and an electrical apparatus, and particularly relates to an ion-generating device in which a positive ion-generating unit and a negative ion-generating unit are disposed, and an electrical apparatus provided with the ion-generating device.

BACKGROUND ART

Many ion-generating devices that utilize a discharge phenomenon have been commercialized. These ion-generating devices are generally configured with an ion-generating element for generating ions, a high-voltage transformer for supplying a high voltage to the ion-generating element, a high voltage-generating circuit for driving the high-voltage transformer, and a power supply input unit such as a connector.

An example of the commercialized ion-generating elements includes the one that uses a metal wire, a metal plate having an acute-angled portion, a needle-like metal, or the like as a discharge electrode, and uses a metal plate, a grid, or the like at a ground potential as an induction electrode (counter electrode), or the one that uses the ground as an induction electrode and does not particularly dispose an induction electrode. In the ion-generating element of this type, the air serves as an insulator. This ion-generating element utilizes a scheme to produce a discharge phenomenon by causing electric field concentration at a tip of an electrode, which has as an acute-angled portion such as a needle-like portion to serve as a discharge electrode, when applying a high voltage to the electrode, and causing an electrical breakdown of the air in close vicinity of the tip.

An example of the ion-generating elements that utilize this scheme is a device disclosed in, for example, Japanese Patent Laying-Open No. 10-199653. This publication discloses a device which includes a discharge electrode provided with a needle-like metal, and a flat-plate electrode with a hole, provided to face the discharge electrode, and serves for extracting negative ions generated as corona discharge occurs, to an outside of the device.

Another example is a device disclosed in, for example, Japanese Patent Laying-Open No. 8-255668. This publication discloses a device which has a positive discharge electrode, a negative discharge electrode, and a ground electrode adjacent to both of the discharge electrodes, and serves for emitting both of positive ions and negative ions to an outside of the ion-producing device.

Still another example is a device disclosed in, for example, Japanese Patent Laying-Open No. 2002-374670. This publication discloses an ion-generating device of the type provided with an ion-generating electrode serving as a discharge electrode and not provided with an induction electrode.

DOCUMENT LIST

Patent Document

Patent Document 1: Japanese Patent Laying-Open No. 10-199653
Patent Document 2: Japanese Patent Laying-Open No. 8-255668
Patent Document 3: Japanese Patent Laying-Open No. 2002-374670

SUMMARY OF THE INVENTION

Problems to be Solved by the Invention

By generating approximately equal amounts of positive ions and negative ions in the air, both types of ions surround funguses and viruses floating in the air, so that it becomes possible to eliminate the floating funguses and others.

However, the device disclosed in Japanese Patent Laying-Open No. 10-199653 is intended to extract only negative ions to an outside of the device, and is not intended to extract both of positive ions and negative ions to an outside of the device.

In the device disclosed in Japanese Patent Laying-Open No. 8-255668, the ground electrode common to both of the positive discharge electrode and the negative discharge electrode is disposed between these discharge electrodes. Therefore, when the distance between these two discharge electrodes is increased, size reduction of the ion-producing device becomes difficult. In contrast, when the positive discharge electrode and the negative discharge electrode are disposed too closely, positive ions and negative ions are neutralized by and recombined with each other, and thus efficient ion emission cannot be achieved.

The device disclosed in Japanese Patent Laying-Open No. 2002-374670 is intended to generate any one type of negative ions and positive ions, and is not intended to generate both of positive ions and negative ions.

The present invention has been made in view of the above-described problems, and an object of the present invention is to provide an ion-generating device and an electrical apparatus, capable of efficiently emitting both of positive ions and negative ions to an outside of the device, and easily achieving reduction in size and thickness.

Means for Solving the Problems

One ion-generating device in the present invention includes: a positive ion-generating unit; and a negative ion-generating unit. The positive ion-generating unit includes a positive discharge electrode, and a first induction electrode for generating positive ions between the first induction electrode and the positive discharge electrode. The negative ion-generating unit includes a negative discharge electrode, and a second induction electrode for generating negative ions between the second induction electrode and the negative discharge electrode. The positive ion-generating unit and the negative ion-generating unit are disposed with a space interposed therebetween, such that the first induction electrode and the second induction electrode are separated from each other.

Another ion-generating device in the present invention includes: a positive ion-generating unit; and a negative ion-generating unit. The positive ion-generating unit includes a positive discharge electrode, and a first induction electrode for generating positive ions between the first induction electrode and the positive discharge electrode. The negative ion-generating unit includes a negative discharge electrode, and a second induction electrode for generating negative ions between the second induction electrode and the negative discharge electrode. The positive ion-generating unit and the negative ion-generating unit are disposed with a space interposed therebetween, by allowing the first induction electrode and the second induction electrode to be spaced apart.

Still another ion-generating device in the present invention includes: a positive ion-generating unit; and a negative ion-generating unit, in a body. The positive ion-generating unit is for generating positive ions, and includes a first induction electrode disposed such that a positive discharge electrode is dischargeable. The negative ion-generating unit is for generating negative ions, and includes a second induction electrode disposed such that a negative discharge electrode is dischargeable. The positive ion-generating unit and the negative ion-generating unit are disposed with a space interposed therebetween, the space being for preventing the generated positive ions and the generated negative ions from being neutralized by each other.

A further ion-generating device in the present invention includes: a positive ion-generating unit; and a negative ion-generating unit, in a body. The positive ion-generating unit is for generating positive ions, and is disposed such that a positive discharge electrode is dischargeable. The negative ion-generating unit is for generating negative ions, and is disposed such that a negative discharge electrode is dischargeable. The positive ion-generating unit and the negative ion-generating unit are disposed with a space interposed therebetween, the space being for preventing the generated positive ions and the generated negative ions from being neutralized by each other.

According to each of the four ion-generating devices described above in the present invention, the positive ion-generating unit and the negative ion-generating unit are disposed with a space interposed therebetween, so that the positive ion-generating unit and the negative ion-generating unit can be disposed separately from each other. It is thereby possible to suppress mutual neutralization of the positive ions generated at the positive ion-generating unit and the negative ions generated at the negative ion-generating unit, and thus efficiently emit both of the positive ions and the negative ions to an outside of the device.

Further, the positive ion-generating unit and the negative ion-generating unit are disposed with a space interposed therebetween, so that another circuit and the like can be disposed in this space. Therefore, it is possible to efficiently dispose respective components, and it becomes easy to achieve reduction in size and thickness of the device.

Preferably, the above-described ion-generating devices further include a first substrate holding both of the positive discharge electrode and the first induction electrode, and a second substrate holding both of the negative discharge electrode and the second induction electrode. The positive ion-generating unit and the negative ion-generating unit are disposed with the above-described space interposed therebetween, such that the first substrate and the second substrate are separated from each other.

As such, the first substrate and the second substrate are separated from each other, and the first and second induction electrodes are separated from each other, so that a space can be made between the positive ion-generating unit and the negative ion-generating unit.

Preferably, the above-described ion-generating devices further include a circuit unit having a portion disposed in the above-described space between the positive ion-generating unit and the negative ion-generating unit.

It is thereby possible to effectively utilize an unused space between the positive ion-generating unit and the negative ion-generating unit, and it becomes easy to achieve reduction in size and thickness of the device.

Preferably, in the above-described ion-generating devices, the circuit unit includes a high voltage-generating circuit for applying a voltage to each of the positive ion-generating unit and the negative ion-generating unit. At least a part of the high voltage-generating circuit is disposed in the space between the positive ion-generating unit and the negative ion-generating unit.

If a wiring extending from the high voltage-generating circuit to each of the ion-generating units is long, a large capacitance is generated at the wiring, so that a value of the voltage applied to the ion-generating units is decreased. According to the above-described ion-generating device, however, the high voltage-generating circuit is disposed in the space between the positive ion-generating unit and the negative ion-generating unit, so that it is possible to reduce the length of the wiring routed from the high voltage-generating circuit to each of the positive ion-generating unit and the negative ion-generating unit, and allow these wirings to have the same distance as much as possible. It is thereby possible to suppress decrease in value of the voltage to be applied to each of the positive ion-generating unit and the negative ion-generating unit, and it is possible to apply approximately the same voltage to the positive ion-generating unit and the negative ion-generating unit.

Preferably, the above-described ion-generating devices further include a casing in which the positive ion-generating unit, the negative ion-generating unit, and the circuit unit are disposed. The casing has a first partition for isolating a region for disposing the positive ion-generating unit from a region for disposing the circuit unit, and a second partition for isolating a region for disposing the negative ion-generating unit from each of the region for disposing the positive ion-generating unit and the region for disposing the circuit unit.

It is thereby possible to mold the entire circuit unit in the region for disposing the circuit unit, for example, and also possible to mold the back surface side of each of the ion-generating units without molding a portion of the ion-generating units isolated by the first and second partitions in the regions for disposing the positive and negative ion-generating units. It is thereby possible to efficiently separate a high-voltage portion of the ion-generating device with a molding compound in an insulating manner, so that it becomes possible to dispose the respective units closely, and hence achieve reduction in size and thickness of the ion-generating device.

Preferably, in the above-described ion-generating devices, the circuit unit includes a power supply circuit for providing an input voltage to the high voltage-generating circuit and driving the high voltage-generating circuit. The ion-generating devices further include a power supply input connector electrically connected to the power supply circuit. The power supply input connector and at least a part of a region for disposing the power supply circuit in the casing are located on any of a side opposite to the above-described space with respect to the positive ion-generating unit and a side opposite to the above-described space with respect to the negative ion-generating unit.

It is thereby possible to dispose the power supply input connector, which is electrically connected to the power supply circuit, separately from both of the region for disposing the positive ion-generating unit and the region for disposing the negative ion-generating unit. It is thereby possible to prevent a lead for connecting to the power supply input connector from disturbing the blown air in the vicinity of the ion-generating units.

Preferably, in the above-described ion-generating devices, a spacing between the positive discharge electrode and the negative discharge electrode is 35 mm or more and 115 mm or less.

If the spacing is less than 35 mm, the probability that positive ions and negative ions are neutralized by and recombined with each other is increased, and efficient ion emission cannot be achieved. In contrast, if the spacing exceeds 115 mm, the ion-generating device is increased in size, and this arrangement becomes similar to that in the case of monopolar ion emission. The monopolar ion emission causes the surroundings to be electrically charged.

Preferably, in the above-described ion-generating devices, the first induction electrode has a first through hole at a position facing a tip of the positive discharge electrode. The second induction electrode has a second through hole at a position facing a tip of the negative discharge electrode. A ratio of a spacing between the positive discharge electrode and the negative discharge electrode with respect to each of a diameter of the first through hole and a diameter of the second through hole is 3 or more and 9.5 or less.

The present inventor has found from earnest studies that, by setting the ratio of the spacing between the positive discharge electrode and the negative discharge electrode with respect to each of the diameter of the first through hole and the diameter of the second through hole to be 3 or more and 9.5 or less, it is possible to efficiently generate and emit bipolar ions, namely, positive ions and negative ions, while achieving reduction in size and thickness of the ion-generating device. The reason can be as follows.

If the spacing between the positive discharge electrode and the negative discharge electrode is as small as to allow the above-described ratio to be less than 3, the probability that positive ions and negative ions are neutralized and recombined is increased, so that bipolar ions, namely, positive ions and negative ions cannot efficiently be generated. In contrast, if each of the diameters of the first and second through holes is as large as to allow the above-described ratio to be less than 3, the distance between the discharge electrode and the induction electrode is increased, so that the required voltage to be applied becomes high and the circuit size is increased, resulting in an increased size of the entire ion-generating device. In other words, it is not possible to efficiently generate ions while achieving reduction in size and thickness.

If the spacing between the positive discharge electrode and the negative discharge electrode is as large as to allow the above-described ratio to exceed 9.5, the distance between the positive discharge electrode and the negative discharge electrode becomes excessively long and the width of the ion-generating device itself is increased. Therefore, the air-blowing condition is deteriorated and it is not possible to efficiently emit bipolar ions, namely, positive ions and negative ions to an outside of the device. Furthermore, if the above-described spacing is large, the positive discharge electrode and the negative discharge electrode become remote, and this arrangement becomes similar to that in the case of monopolar ion emission, and the monopolar ion emission causes the surroundings to be electrically charged. If each of the diameters of the first and second through holes is as small as to allow the above-described ratio to exceed 9.5, the range between the discharge start voltage and the spark discharge transition voltage becomes small, which makes it difficult to set a voltage to be applied, resulting in a failure of efficient ion generation. Furthermore, the generated ions are emitted to an outside of the ion-generating elements through the first and second through holes, and hence if each of the diameters of the first and second through holes is as small as to allow the above-described ratio to exceed 9.5, the ions cannot efficiently be emitted to the outside of the ion-generating elements.

In view of the correspondence between each of the diameters of the first and second holes and the spacing between the positive discharge electrode and the negative discharge electrode, as described above, the relevant ratio of 3 or more and 9.5 or less is considered to enable efficient generation and emission of bipolar ions, namely, positive ions and negative ions, while enabling reduction in size and thickness of the ion-generating device.

An electrical apparatus in the present invention includes: any of the above-described ion-generating devices; and an air blow unit for delivering both of the positive ions and the negative ions generated at the ion-generating device on a blown air stream to an outside of the electrical apparatus.

According to the electrical apparatus in the present invention, the ions generated at the ion-generating device can be delivered on an air stream by the air blow unit, so that it is possible to, for example, emit ions to an outside of an air-conditioning apparatus, and emit ions to an inside and an outside of a cooling apparatus.

Effects of the Invention

As described above, according to the present invention, it is possible to efficiently emit both of positive ions and negative ions to an outside of the device, and easily achieve reduction in size and thickness.

MODES FOR CARRYING OUT THE INVENTION

Embodiments of the present invention will hereinafter be described based on the drawings.

(First Embodiment)

Figure 1:
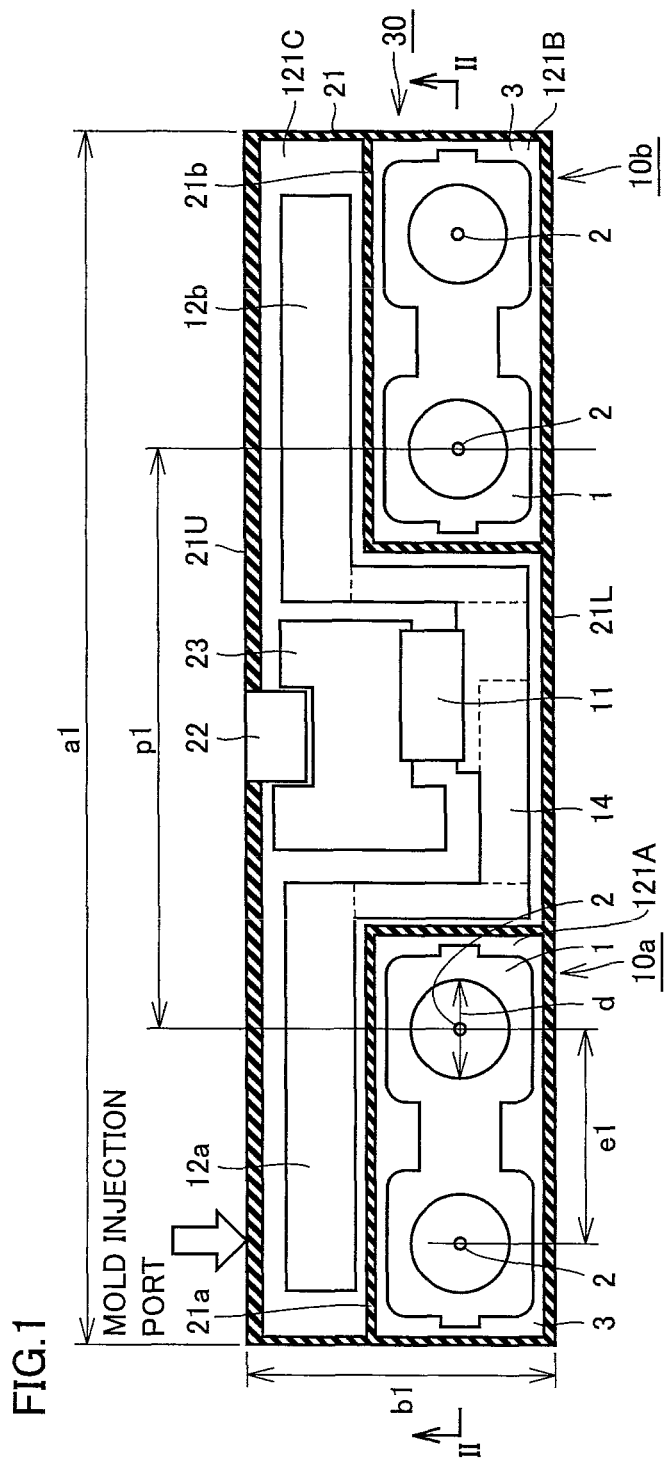
FIG. 1 is a schematic plan view of a configuration of an ion-generating device in a first embodiment of the present invention, when seen from a bottom surface side of a casing, and shows a bottom plate portion of the casing and a molding resin in perspective.
Figure 2:
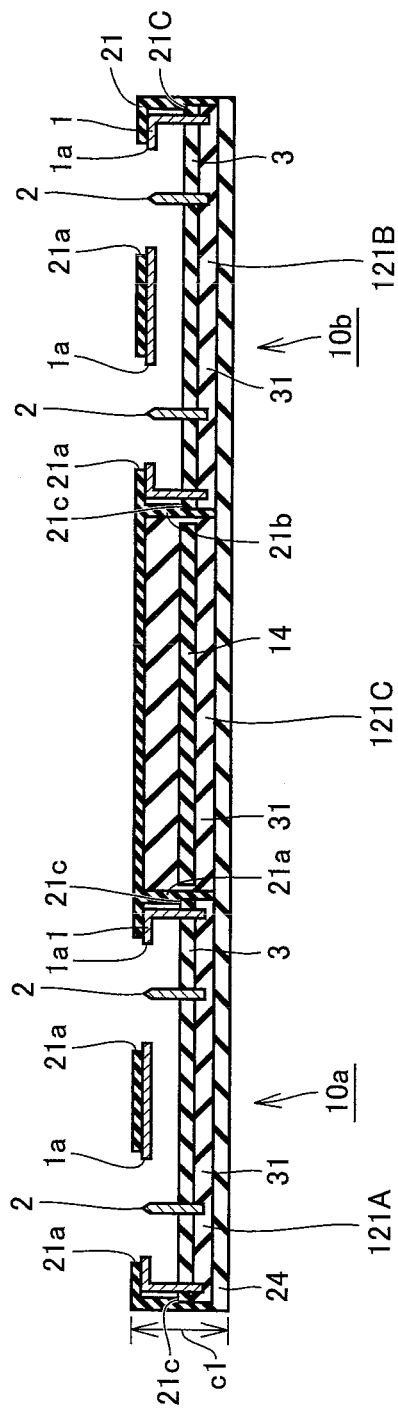
FIG. 2 is a schematic cross-sectional view taken along a line II-II in FIG. 1.
Figure 3:
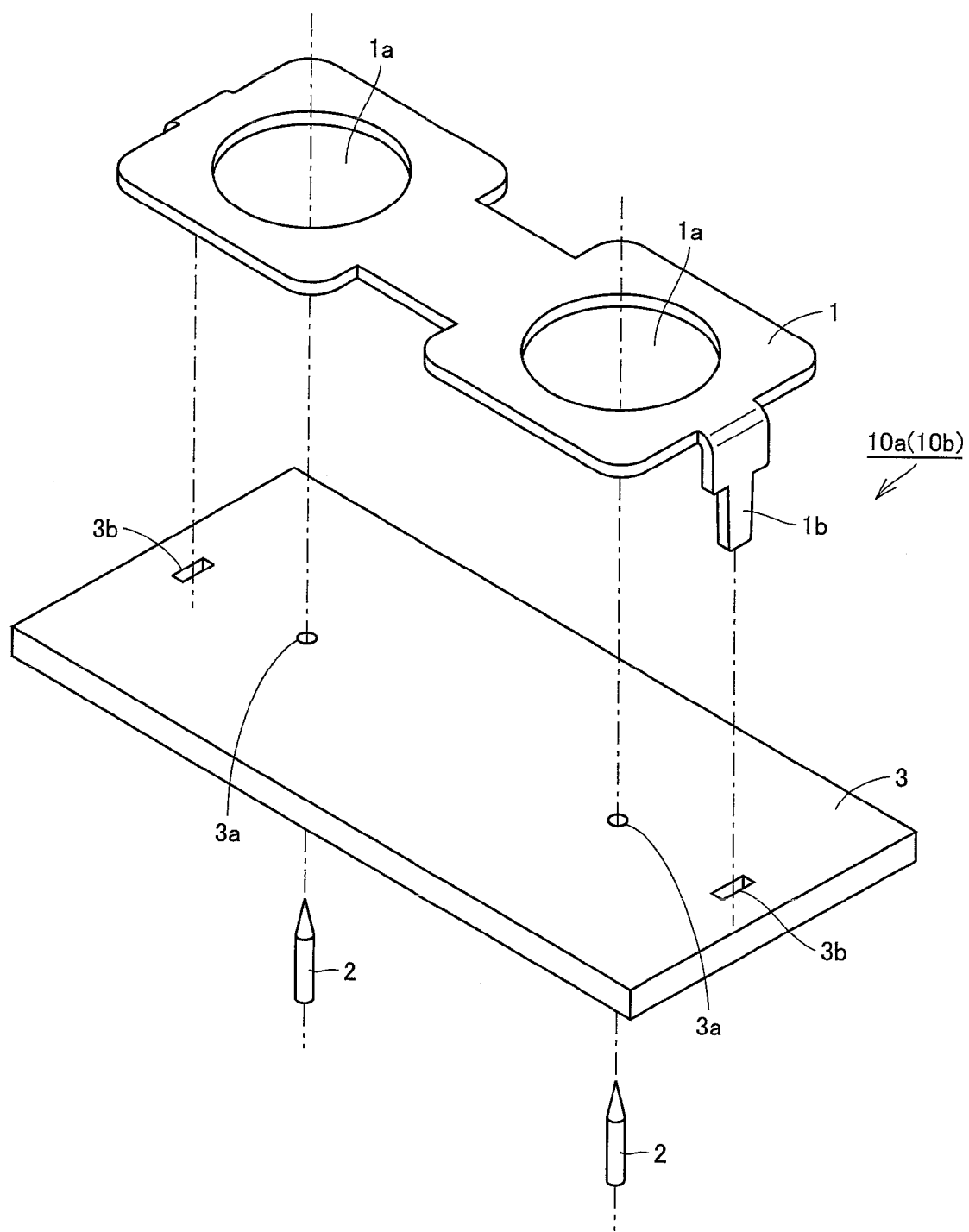
FIG. 3 is an exploded perspective view that shows a configuration of an ion-generating element shown in FIGS. 1 and 2.
Figure 4:
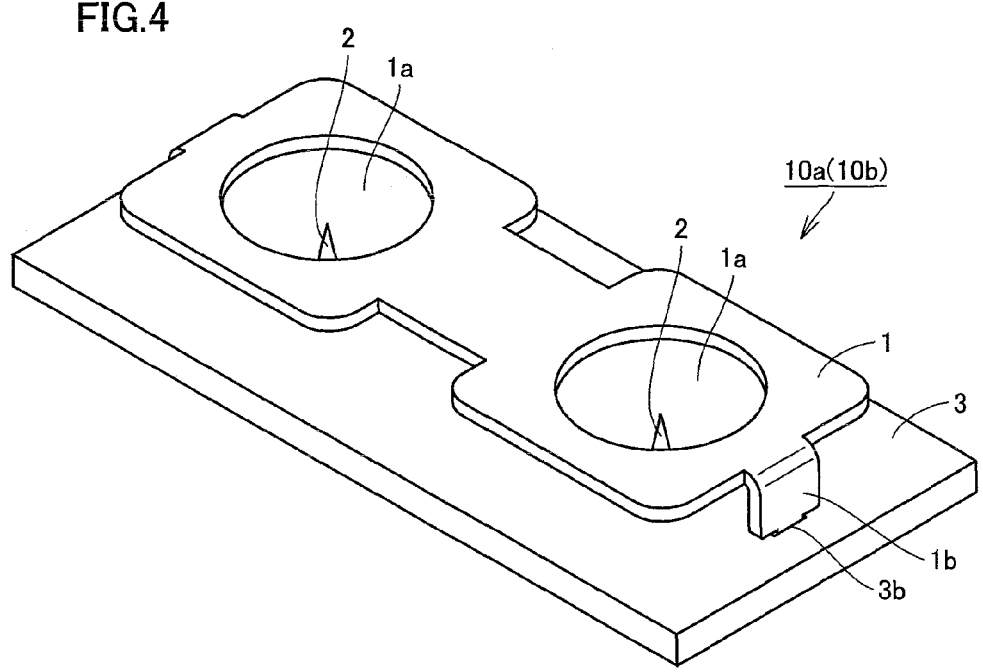
FIG. 4 is a perspective assembly view that shows the configuration of the ion-generating element shown in FIGS. 1 and 2.

FIG. 1 is a schematic plan view of a configuration of an ion-generating device in a first embodiment of the present invention, when seen from a bottom surface side of a casing, and shows a bottom plate portion of the casing and a molding resin in perspective. FIG. 2 is a schematic cross-sectional view taken along a line II-II in FIG. 1. FIGS. 3 and 4 are an exploded perspective view and a perspective assembly view, respectively, that show a configuration of an ion-generating element shown in FIGS. 1 and 2.

With reference to FIG. 1, an ion-generating device 30 in the present embodiment mainly has an outer casing 21, an ion-generating element 10a for generating positive ions, an ion-generating element 10b for generating negative ions, a high-voltage transformer 11, high-voltage circuits 12a, 12b, a power supply circuit 23, and a power supply input connector 22.

Outer casing 21 has a first partition 21a and a second partition 21b in itself. An inside of outer casing 21 is partitioned by first partition 21a and second partition 21b into a region 121A for disposing the positive ion-generating element, a region 121B for disposing the negative ion-generating element, and a region 121C for disposing a high voltage-generating circuit and the like.

Region 121A for disposing the positive ion-generating element is disposed on a one end side (on the left in FIG. 1) in casing 21, and region 121B for disposing the negative ion-generating element is disposed on the other end side (on the right in FIG. 1) in casing 21. Between region 121A for disposing the positive ion-generating element and region 121B for disposing the negative ion-generating element, a part of region 121C for disposing the high voltage-generating circuit and the like is interposed.

Ion-generating element 10a for generating positive ions is disposed in region 121A for disposing the positive ion-generating element, and ion-generating element 10b for generating negative ions is disposed in region 121B for disposing the negative ion-generating element.

With reference to FIGS. 3 and 4, ion-generating elements 10a, 10b are for generating positive ions and negative ions, respectively, by corona discharge, for example, and have an induction electrode 1, a discharge electrode 2, and a supporting substrate 3.

Induction electrode 1 is made of a one-piece metal plate, and has a plurality of (e.g. two) circular through holes 1a provided at a flat plate portion to correspond to the number of discharge electrodes 2. Through hole 1a is an opening for emitting ions generated by corona discharge to an outside of ion-generating element 10a or 10b. The flat plate portion of induction electrode 1 is made of a sheet metal with a hole.

Induction electrode 1 has a bent portion 1b at each of opposite end portions, bent portion 1b being made by bending a part of the metal plate at approximately a right angle with respect to the flat plate portion. Bent portion 1b has a large-width supporting portion and a small-width inserted portion. The above-described supporting portion has one end linked to the flat plate portion, and the other end linked to the above-described inserted portion.

Discharge electrode 2 has a needle-like tip. Supporting substrate 3 has a through hole 3a for allowing discharge electrode 2 to be inserted therethrough, and a through hole 3b for allowing the inserted portion of bent portion 1b to be inserted therethrough.

Needle-like discharge electrode 2 is supported by supporting substrate 3 while being inserted or press-fitted into through hole 3a and penetrating supporting substrate 3. Consequently, one end of discharge electrode 2, which is a needle-like end, protrudes on a front surface side of supporting substrate 3. To the other end of discharge electrode 2, which protrudes on a back surface side of supporting substrate 3, it is possible to electrically connect a lead wire or a wiring pattern with use of solder (not shown).

The inserted portion of induction electrode 1 is supported by supporting substrate 3 while being inserted into through hole 3b and penetrating supporting substrate 3. To a tip of the inserted portion, which protrudes on the back surface side of supporting substrate 3, it is possible to electrically connect a lead wire or a wiring pattern with use of solder (not shown). Further, in the state where induction electrode 1 is supported by supporting substrate 3, discharge electrode 2 is disposed such that its needle-like tip is located approximately at the center of circular through hole 1a as shown in FIG. 1.

Discharge electrode 2 in ion-generating element 10a for generating positive ions serves as a positive discharge electrode, and cooperates with induction electrode 1 in ion-generating element 10a to configure a positive ion-generating unit (positive electrode pair). Discharge electrode 2 in ion-generating element 10b for generating negative ions serves as a negative discharge electrode, and cooperates with induction electrode 1 in ion-generating element 10b to configure a negative ion-generating unit (negative electrode pair).

Further, common induction electrode 1 is provided for the plurality of discharge electrodes 2 for generating ions of the same polarity, namely, a positive polarity or a negative polarity. Specifically, in ion-generating element 10a for generating positive ions, common induction electrode 1 is provided for two positive discharge electrodes 2, for example, and induction electrode 1 is provided with two through holes 1a to correspond to the number of positive discharge electrodes 2. As such, ion-generating element 10a for generating positive ions is configured to be able to generate positive ions at a plurality of (e.g. two) positive ion-generating units.

In ion-generating element 10b for generating negative ions, common induction electrode 1 is provided for two negative discharge electrodes 2, for example, and induction electrode 1 is provided with two through holes 1a to correspond to the number of negative discharge electrodes 2. As such, ion-generating element 10b for generating negative ions is configured to be able to generate negative ions at a plurality of (e.g. two) negative ion-generating units.

With reference to FIG. 1, ion-generating element 10a for generating positive ions located in region 121A for disposing the positive ion-generating element, and ion-generating element 10b for generating negative ions located in region 121B for disposing the negative ion-generating element are disposed in casing 21 with a space interposed therebetween. In other words, the positive ion-generating units and the negative ion-generating units are disposed in casing 21 with a space interposed therebetween.

Further, induction electrode 1 in ion-generating element 10a for generating positive ions and induction electrode 1 in ion-generating element 10b for generating negative ions are spatially (structurally) separated from each other. Further, supporting substrate 3 in ion-generating element 10a for generating positive ions and supporting substrate 3 in ion-generating element 10b for generating negative ions are spatially (structurally) separated from each other. It is noted that induction electrode 1 in ion-generating element 10a for generating positive ions and induction electrode 1 in ion-generating element 10b for generating negative ions may electrically be connected to each other such that they are at the same potential.

High-voltage transformer 11, high-voltage circuits 12a, 12b, power supply circuit 23, and power supply input connector 22 are disposed in region 121C for disposing a high voltage-generating circuit and the like. Both of positive high-voltage circuit 12a and negative high-voltage circuit 12b are supported on the same substrate 14. Positive high-voltage circuit 12a is disposed in casing 21 on one end side (on the left in FIG. 1) such that it is adjacent to ion-generating element 10a for generating positive ions. Negative high-voltage circuit 12b is disposed in casing 21 on the other end side (on the right in FIG. 1) such that it is adjacent to ion-generating element 10b for generating negative ions. A part of substrate 14 supporting high-voltage circuits 12a, 12b is located between region 121A for disposing the positive ion-generating element and region 121B for disposing the negative ion-generating element.

High-voltage transformer 11, power supply circuit 23, and power supply input connector 22 are further disposed between region 121A for disposing the positive ion-generating element and region 121B for disposing the negative ion-generating element. In particular, power supply input connector 22 is disposed approximately at the center between region 121A for disposing the positive ion-generating element and region 121B for disposing the negative ion-generating element. High-voltage transformer 11 and high-voltage circuits 12a, 12b as described above configure a high voltage-generating circuit 20. High voltage-generating circuit 20 and power supply circuit 23 configure a circuit unit.

In a planar layout in FIG. 1, an arrangement of ion-generating element 10a/the circuit unit/the ion-generating element 10b is adopted from the left to the right in FIG. 1.

With reference to FIG. 2, casing 21 is a box-type one having a space therein. In the space in casing 21, ion-generating elements 10a, 10b, high-voltage transformer 11, high-voltage circuits 12a, 12b, power supply circuit 23, and power supply input connector 22 are disposed. After a lid 24 is attached, a molding resin 31 is poured thereinto.

Casing 21 has an ion emission hole 21d at, for example, a box-type bottom plate. Each of ion-generating elements 10a, 10b is disposed in casing 21 such that each of through holes 1a of ion-generating elements 10a, 10b is brought into communication with hole 21d.

Soldering surface side of each of ion-generating elements 10a, 10b and region 121C for disposing the high voltage-generating circuit and the like are molded with a molding resin 31. Here, high voltage-generating circuit 20 configured with high-voltage transformer 11 and high-voltage circuits 12a, 12b, and ion-generating elements 10a, 10b serve as a high-voltage unit. Therefore, it is preferable to reinforce insulation by subjecting the back surface side (the soldering surface side) of supporting substrate 3 and the region for disposing the high voltage-generating circuit and the like to resin molding (e.g. molding with use of an epoxy resin), except for the ion-generating portions of ion-generating elements 10a, 10b (i.e. the front surface side of supporting substrate 3).

In the present embodiment, casing 21 has a step 21c which abuts against supporting substrate 3 of each of ion-generating elements 10a, 10b when ion-generating elements 10a, 10b are disposed in casing 21. By allowing supporting substrate 3 to abut against step 21c, supporting substrate 3 is positioned, and additionally, a resin is prevented from flowing toward the ion-generating unit side during the molding. It is thereby possible, in a single molding step, to mold the entire high voltage-generating circuit in the region for disposing the high voltage-generating circuit, and mold only a side of supporting substrate 3 of each of ion-generating elements 10a, 10b, which side is opposite to the ion-generating portion side, without molding the ion-generating portion side.

With reference to FIG. 1, in the present embodiment, a ratio (p1/d) of a spacing p1 between positive discharge electrode 2 and negative discharge electrode 2 with respect to a diameter d of through hole 1a is 3 or more and 9.5 or less, and an example of the ratio is 7.4.

Further, diameter d of through hole 1a is preferably $\phi 10$ mm-$\phi 15$ mm, spacing p1 between positive discharge electrode 2 and negative discharge electrode 2 is preferably d<p1<150 mm, and preferably 35-115 mm. An external shape of outer casing 21 is defined by a length a1 (FIG. 1)×a width b1 (FIG. 1)×a thickness c1 (FIG. 2), and preferably has a thin and compact shape having a1 of 70-150 mm, b1 of 20-40 mm, and c1 of 8-10 mm.

Next, description will be made on how respective functional elements are electrically connected.

Figure 5:
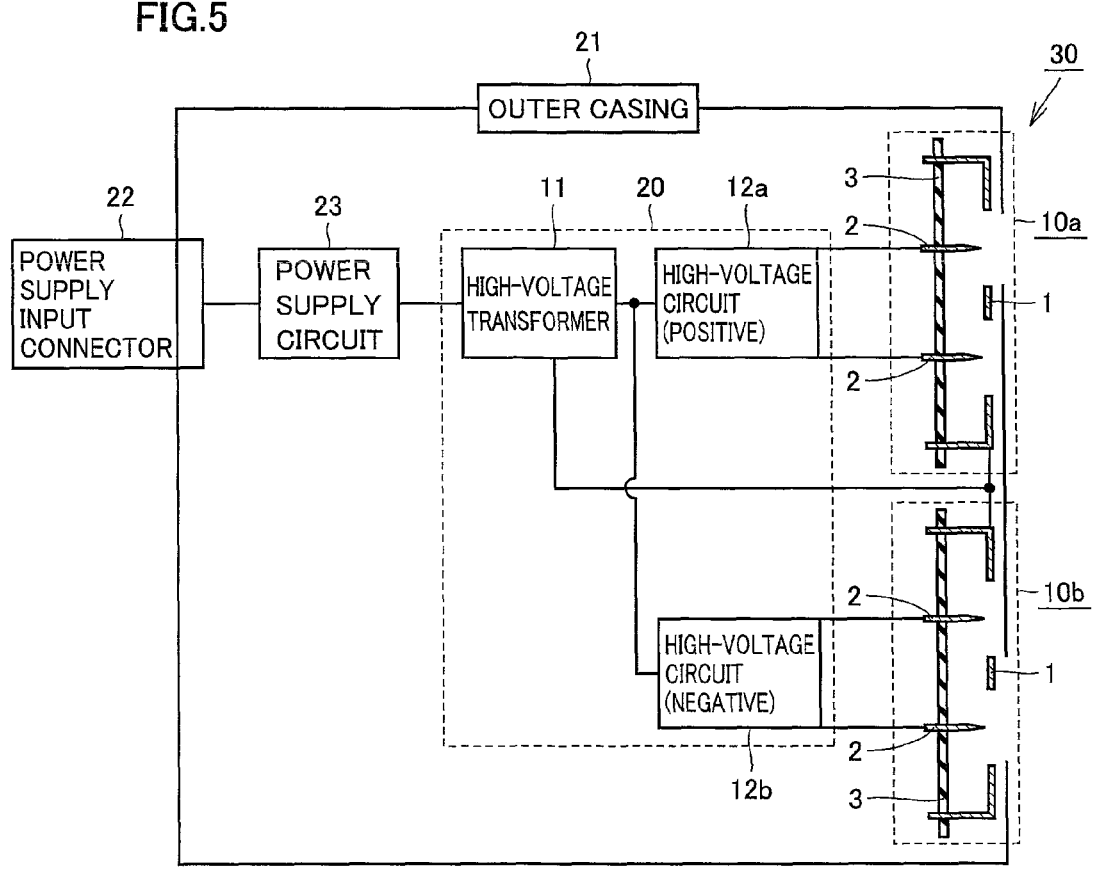
FIG. 5 is a functional block diagram of the ion-generating device in the first embodiment of the present invention, and shows how the functional elements are electrically connected.

FIG. 5 is a functional block diagram of the ion-generating device in the first embodiment of the present invention, and shows how the functional elements are electrically connected. With reference to FIG. 5, ion-generating device 30 includes outer casing 21, ion-generating elements 10a, 10b, high-voltage transformer 11, high-voltage circuits 12a, 12b, power supply input connector 22, and power supply circuit 23, as described above. It is noted that power supply input connector 22 is structured such that a part thereof is disposed in outer casing 21, and another part thereof is exposed to an outside of outer casing 21, to thereby allow a power supply to be connected from an outside.

Power supply input connector 22 is a portion for receiving a direct-current power supply or a commercial alternating-current power supply, which serves as an input power supply. Power supply input connector 22 is electrically connected to power supply circuit 23. Power supply circuit 23 is electrically connected to a primary side of high-voltage transformer 11. High-voltage transformer 11 is for stepping up a voltage inputted to the primary side, and outputting the stepped-up voltage to the secondary side. One end of the secondary side of high-voltage transformer 11 is electrically connected to induction electrode 1 of each of ion-generating elements 10a, 10b. The other end of the secondary side of high-voltage transformer 11 is electrically connected via positive high-voltage circuit 12a to positive discharge electrodes 2 of ion-generating element 10a for generating positive ions, and electrically connected via negative high-voltage circuit 12b to negative discharge electrodes 2 of ion-generating element 10b for generating negative ions.

Positive high-voltage circuit 12a is configured to apply to positive discharge electrode 2 a high voltage having a positive polarity with respect to induction electrode 1, and negative high-voltage circuit 12b is configured to apply to negative discharge electrode 2 a high voltage having a negative polarity with respect to induction electrode 1. It is thereby possible to generate dual-polarity ions, namely, positive ions and negative ions.

Next, description will be made on a configuration of the bottom plate of the casing in the present embodiment.

Figure 6:
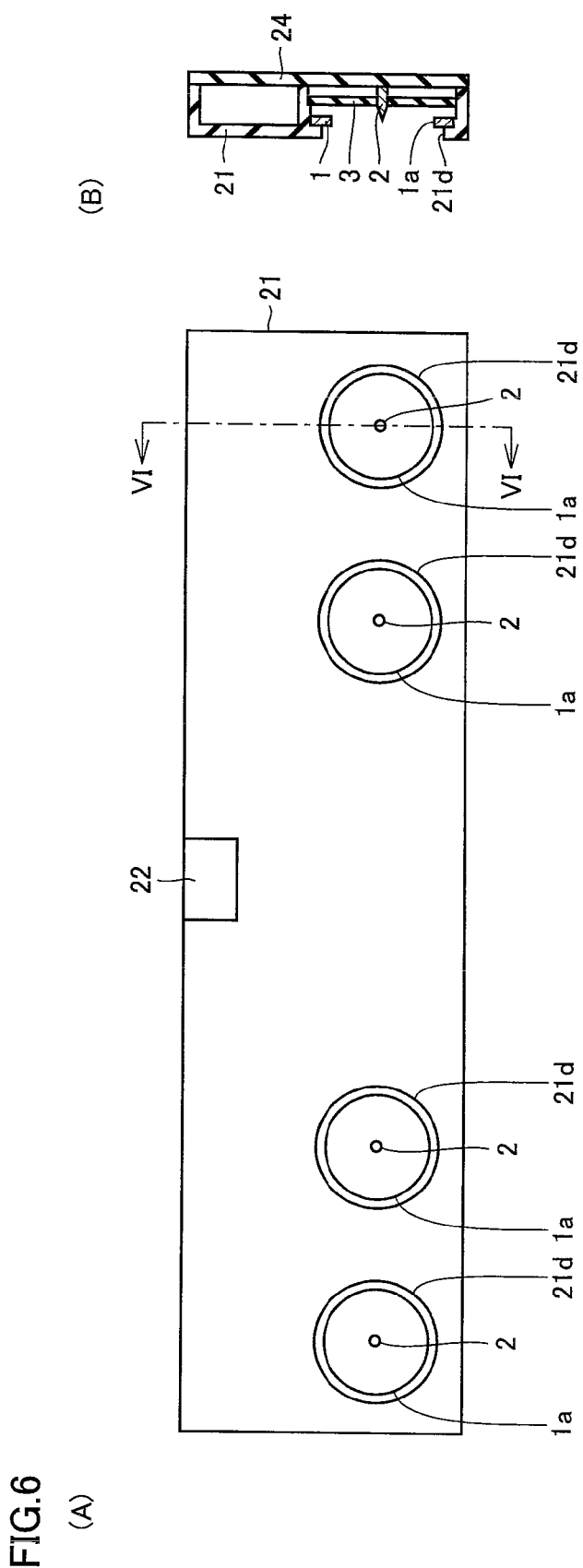
FIG. 6 (A) is a schematic plan view that shows a configuration of a bottom plate of the casing in the ion-generating device in the first embodiment of the present invention, and FIG. 6 (B) is a schematic cross-sectional view taken along a line VI-VI in FIG. 6 (A).

As shown in the plan view in FIG. 6 (A) and the cross-sectional view in FIG. 6 (B), ion emission hole 21d is formed at the bottom plate of the casing. Ion emission hole 21d is disposed immediately above through hole 1a of induction electrode 1. It is thereby possible to see discharge electrode 2 from an outside of ion-generating device 30 via ion emission hole 21d and through hole 1a, and emit ions generated at ion-generating elements 10a, 10b to the outside of ion-generating device 30.

Figure 7:
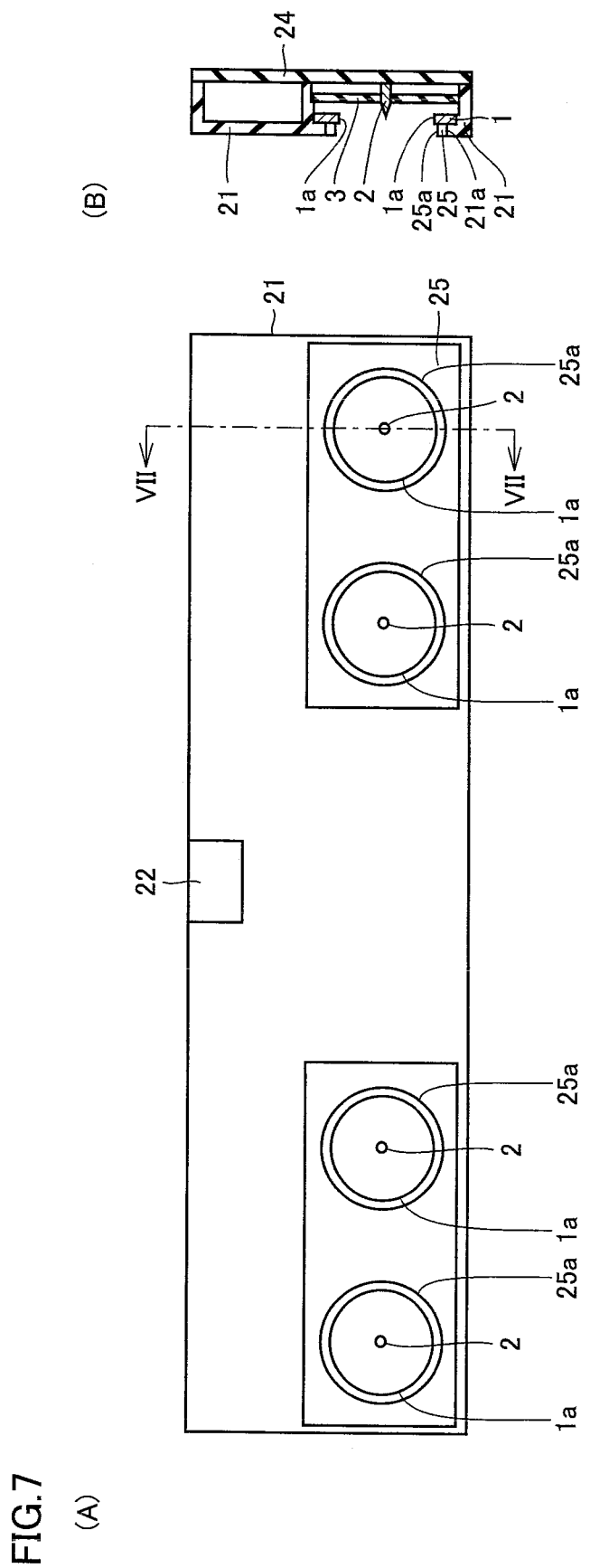
FIG. 7 (A) is a schematic plan view that shows a configuration in which a part of the bottom plate of the casing is made of an electrode lid detachable from the bottom plate, and FIG. 7 (B) is a schematic cross-sectional view taken along a line VII-VII in FIG. 7 (A).

Alternatively, as shown in the plan view in FIG. 7 (A) and the cross-sectional view in FIG. 7 (B), a part of the bottom plate of casing 21 may be made of an electrode lid 25 which has a structure detachable from the bottom plate. Electrode lid 25 has an ion emission hole 25a formed thereat.

It is noted that the cross-sectional view in FIG. 6 (B) is a schematic cross-sectional view taken along a line VI-VI in FIG. 6 (A), and the cross-sectional view in FIG. 7 (B) is a schematic cross-sectional view taken along a line VII-VII in FIG. 7 (A).

Although ion-generating device 30 described above can emit single-polarity ions, the present embodiment is based on the premise that bipolar ions, namely, positive ions and negative ions are emitted. Positive ions are generated by causing positive corona discharge at the tip of positive discharge electrodes 2, and negative ions are generated by causing negative corona discharge at the tip of negative discharge electrodes 2. A waveform to be applied is not particularly limited herein, and a direct current, an alternating-current waveform biased positively or negatively, a pulse waveform biased positively or negatively, or the like, having a high voltage is used. A voltage value is selected to fall within a voltage range that sufficiently causes discharge and enables generation of prescribed ion species.

Here, positive ions intended by the inventor are cluster ions each of which is identified as a hydrogen ion ($H^+$) having a plurality of water molecules attached therearound, and are represented as $H^+(H_2O)_m$ (m is a natural number). Negative ions are cluster ions each of which is identified as an oxygen ion ($O_2^-$) having a plurality of water molecules attached therearound, and are represented as $O_2^-(H_2O)_n$ is a natural number). Further, by generating approximately the same amount of $H^+(H_2O)_m$ (m is a natural number), which are identified as positive ions in the air, and $O_2^-(H_2O)_n$ (n is a natural number), which are identified as negative ions in the air, both types of ions attach to and surround funguses and viruses floating in the air. With the action of hydroxyl radicals (.OH) generated at that time, which are identified as active species, the floating funguses and others can be eliminated.

Next, description will be made on a configuration of an air-cleaning unit, which is an example of the electrical apparatus that uses the above-described ion-generating device.

Figure 8:
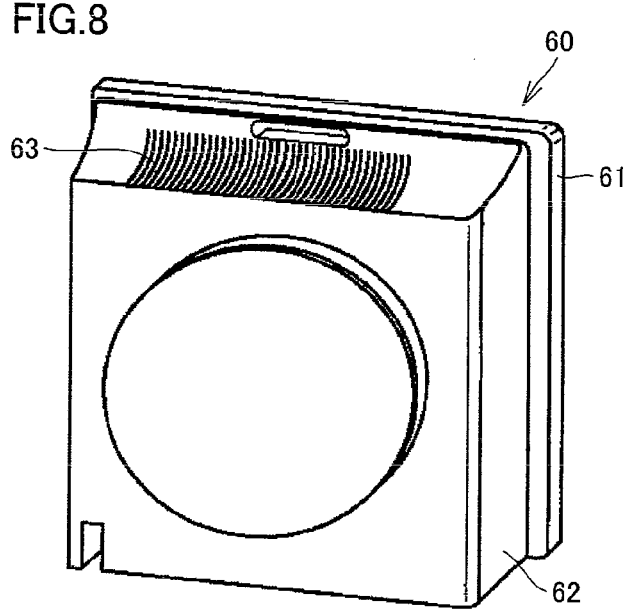
FIG. 8 is a perspective view that schematically shows a configuration of an air-cleaning unit that uses the ion-generating device shown in FIGS. 1 and 2.
Figure 9:
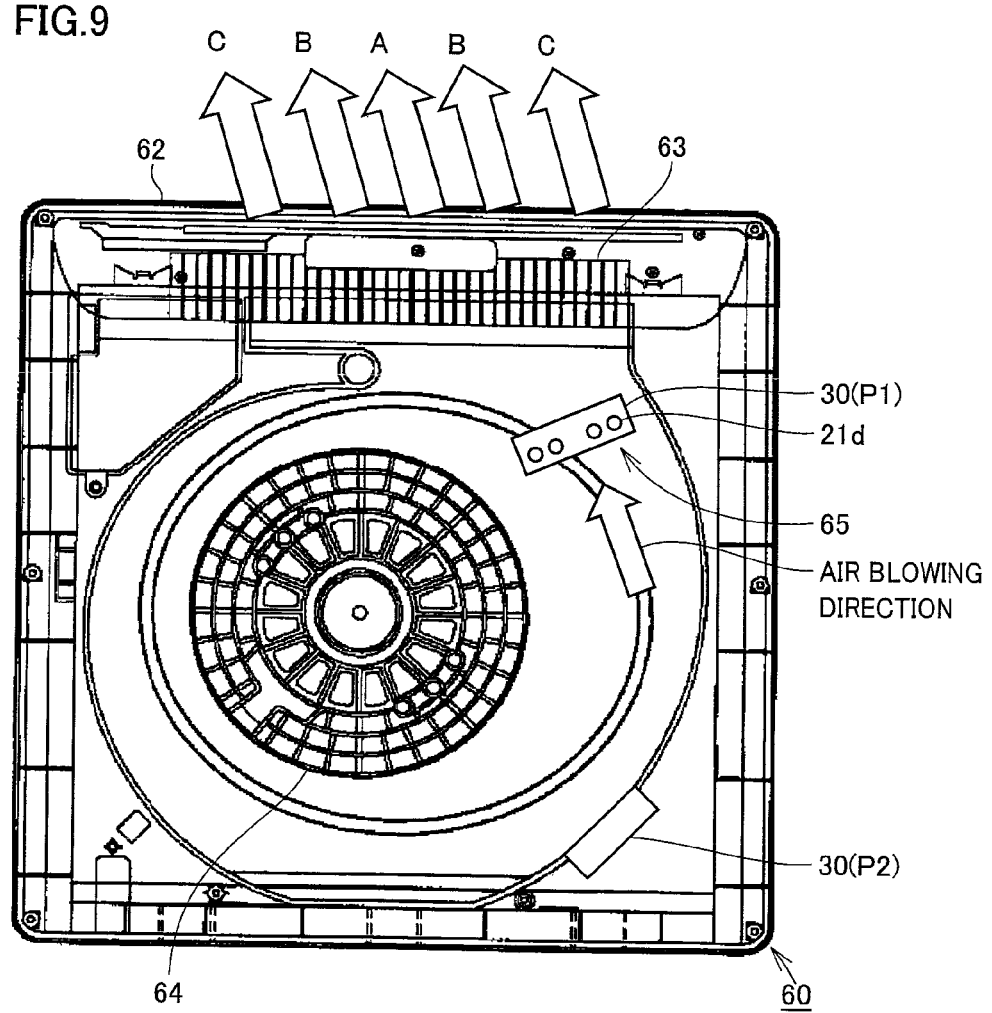
FIG. 9 is an exploded view of the air-cleaning unit, showing how the ion-generating device is disposed in the air-cleaning unit shown in FIG. 8.

FIG. 8 is a perspective view that schematically shows a configuration of an air-cleaning unit that uses the ion-generating device shown in FIGS. 1 and 2. FIG. 9 is an exploded view of the air-cleaning unit shown in FIG. 8, showing how the ion-generating device is disposed in the air-cleaning unit therein.

With reference to FIGS. 8 and 9, an air-cleaning unit 60 has a front panel 61 and a body 62. A rear top portion of body 62 is provided with an outlet port 63, through which clean air containing ions are supplied to the room. An air intake port 64 is formed at the center of body 62. The air taken in through air intake port 64 located at the front of air-cleaning unit 60 is cleaned by passing through a filter not shown. The cleaned air is supplied from outlet port 63 to the outside through a fan casing 65.

Ion-generating device 30 shown in FIGS. 1 and 2 is attached to a part of fan casing 65 that forms a passage of the cleaned air. Ion-generating device 30 is disposed to be able to emit ions through hole 21d, which serves as an ion-emitting unit, onto the flow of the above-described air. Exemplary dispositions of ion-generating device 30 may include a position P1 relatively close to outlet port 63, a position P2 relatively far from outlet port 63, and other positions, within the passage of the air. By allowing the blown air to pass through ion-emitting unit 21d in ion-generating device 30 as such, air-cleaning unit 60 can achieve an ion-generating function, namely, a function of supplying ions, along with clean air, through outlet port 63 to the outside.

With air-cleaning unit 60 according to the present embodiment, both of positive ions and negative ions generated at ion-generating device 30 can be delivered on the air stream by the air blow unit (air passage), so that both of positive ions and negative ions can be emitted to the outside of the unit.

In the present embodiment, an air-cleaning unit has been described as an example of the electrical apparatus. However, the present invention is not limited thereto. The electrical apparatus may also be, in addition to the air-cleaning unit, an air-conditioning unit (air-conditioner), a cooling apparatus, a vacuum cleaner, a humidifier, a dehumidifier, and the like, as long as it is an electrical apparatus that has an air blow unit for delivering ions on the air stream.

Next, description will be made on functional effects of the present embodiment. Positive ions and negative ions generated by discharge disappear by being recombined at a moment of production, by being neutralized when a positively-applied or negatively-applied electrode attracts the ions having a reverse polarity, or by being neutralized by collision between positive ions and negative ions in a space, and the like.

In contrast, in the present embodiment, the positive ion-generating units (positive discharge electrodes 2 and induction electrode 1 in ion-generating element 10a for generating positive ions) and the negative ion-generating units (negative discharge electrodes 2 and induction electrode 1 in ion-generating element 10b for generating negative ions) are disposed in casing 21 with a space (region 121C for disposing the high voltage-generating circuit and the like) interposed therebetween in plan view. Therefore, the positive ion-generating units and the negative ion-generating units can be disposed separately from each other by the relevant space. It is thereby possible to prevent the positive ions generated at the positive ion-generating units and the negative ions generated at the negative ion-generating units from being neutralized by and recombined with each other, and it becomes possible to efficiently emit both of the positive ions and the negative ions to an outside of the device.

Further, the positive ion-generating units and the negative ion-generating units are disposed in casing 21 with a space interposed therebetween, in plan view, so that another circuit such as the high voltage-generating circuit can be disposed in this space. Therefore, it is possible to efficiently dispose the respective components in casing 21, and easily achieve size reduction and compactness of ion-generating device 30. An area to be occupied by ion-generating device 30 itself is thereby reduced, so that the range of uses is increased, and that the limitations to be imposed on the disposition in an electrical apparatus are reduced, when ion-generating device 30 is considered to be mounted on the electrical apparatus.

Further, the positive ion-generating units, the negative ion-generating units, and other circuits disposed in the space can be disposed laterally on a plane, so that the thickness of ion-generating device 30 can also be reduced. Therefore, it is also possible to apply ion-generating device 30 in the present embodiment to an apparatus having a narrow air blow passage, resulting in improvement in general versatility.

Further, induction electrode 1 in ion-generating element 10a for generating positive ions and induction electrode 1 in ion-generating element 10b for generating negative ions are separated spatially from each other, and in addition, supporting substrate 3 in ion-generating element 10a for generating positive ions and supporting substrate 3 in ion-generating element 10b for generating negative ions are separated physically from each other. Therefore, it becomes possible to provide a space between ion-generating element 10a and ion-generating element 10b.

Further, region 121A for disposing ion-generating element 10a and region 121C for disposing the high voltage-generating circuit and the like are separated by partition 21a, and region 121B for disposing ion-generating element 10b and region 121C for disposing the high voltage-generating circuit and the like are separated by partition 21b. Therefore, it is possible to mold the entire high voltage-generating circuit 20 in region 121C for disposing high voltage-generating circuit 20 and the like, for example, and mold only a side of supporting substrate 3, which side is opposite to the ion-generating portion side, without molding the ion-generating portion side, in each of region 121A for disposing positive ion-generating element 10a and region 121B for disposing negative ion-generating element 10b. It is thereby possible to efficiently separate the high-voltage portion of ion-generating device 30 with use of molding resin 31 in an insulating manner, and thus dispose the respective portions more closely, and achieve reduction in size and thickness, and compactness of the ion-generating device.

Molding is conducted by, for example, the following method.

With reference to FIG. 1, a plane 21L of ion-generating device 30, which is located in the lower part of the drawing, is disposed to face downward, and a plane 21U, which is located in the upper part of the drawing, is disposed to face upward. In this state, as shown by a bold arrow in FIG. 1, a molding resin is injected into ion-generating device 30 through a mold injection port provided at upper plane 21U. The molding resin injected into ion-generating device 30 accumulates from the lower part to the upper part of casing 21. At this time, in region 121C for disposing the high voltage-generating circuit and the like, the molding resin flows onto the entire surfaces of high voltage-generating circuit 20 and power supply circuit 23, so that the entire circuits are molded therewith. In contrast, in both of region 121A for disposing ion-generating element 10a and region 121B for disposing ion-generating element 10b, the molding resin cannot flow onto the ion-generating unit side of supporting substrate 3 (i.e. the front surface side of supporting substrate 3) because of partitions 21a, 21b, and coats only the soldering surface side of supporting substrate 3, which side is opposite to the ion-generating unit side.

It is thereby possible to mold, in a single molding step, the high-voltage portion of ion-generating device 30 and avoid molding the ion-generating unit in each of ion-generating elements 10a, 10b.

Further, according to the present embodiment, induction electrode 1 and discharge electrodes 2 are disposed on the same supporting substrate 3. It is thereby possible to minimize displacement in the height direction while regulating a mutual planar displacement between induction electrode 1 and discharge electrodes 2. It is thereby possible to reduce causes of errors in positional relation between induction electrode 1 and discharge electrodes 2.

Further, according to the present embodiment, through hole 1a has a planar shape of approximately a perfect circle, and the needle-like tip of discharge electrode 2 is located at the center of that circle in plan view. Therefore, it is possible to uniformize the electric field generated between induction electrode 1 and discharge electrode 2 over 360 degrees in plan view.

The present inventor has found from earnest studies that it is possible to efficiently generate and emit bipolar ions, namely, positive ions and negative ions, while achieving reduction in size and thickness, and compactness of ion-generating device 30, by setting a ratio ($p1/d$) of spacing $p1$ between positive discharge electrode 2 and negative discharge electrode 2 with respect to diameter $d$ of through hole 1a of each of ion-generating elements 10a, 10b to be 3 or more and 9.5 or less. This feature will hereinafter be described.

To cause stable corona discharge at the tip of discharge electrode 2, a required voltage value of a high voltage to be applied between discharge electrode 2 and induction electrode 1 varies depending on the relation of the distance between the tip of discharge electrode 2 and induction electrode 1 (i.e. a radius ($d/2$) of through hole 1a of induction electrode 1). If a radius ($d/2$) of through hole 1a of induction electrode 1 becomes larger, a required voltage to be applied becomes higher. Therefore, the sizes of high-voltage circuits 12a, 12b and high-voltage transformer 11 become larger and the required power is increased, resulting in a deviation from the viewpoint of reducing size and thickness of ion-generating device 30, which deviation is not preferable. In other words, it is not possible to stably generate ions while maintaining reduced size and thickness.

In contrast, if a radius ($d/2$) of through hole 1a of induction electrode 1 is excessively small, a required voltage to be applied can be lowered. However, the range between a discharge start voltage and a spark discharge transition voltage becomes smaller, which makes it difficult to set a voltage to be applied, and also makes it difficult to achieve stable ion emission by corona discharge.

Based on the above-described studies, the present inventor has further studied the relation between diameter $d$ of through hole 1a of induction electrode 1 and an optimal distance $p1$ between positive discharge electrode 2 and negative discharge electrode 2.

Figure 10:
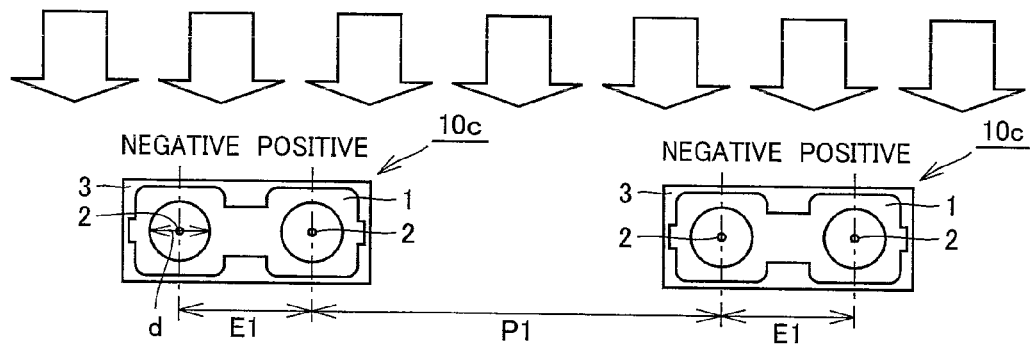
FIG. 10 is a schematic plan view that shows a configuration of two ion-generating elements having a polarity arrangement of negative/positive/negative/positive, which ion-generating elements are prepared for studying the relation between a diameter of a through hole of each of the induction electrodes and an optimal distance between the positive discharge electrode and the negative discharge electrode.

Initially, two ion-generating elements 10c as shown in FIG. 10 were prepared. Each of ion-generating elements 10c was configured to have supporting substrate 3, two discharge electrodes 2 supported by supporting substrate 3, and induction electrode 1 having through holes 1a at positions opposite to the tips of discharge electrodes 2, respectively. In each of ion-generating elements 10c, one of the two discharge electrodes 2 was set to serve as a positive discharge electrode, and the other was set to serve as a negative discharge electrode. Such two ion-generating elements 10c were disposed laterally. At this time, the arrangement of polarity of discharge electrodes 2 was in order of negative/positive/negative/positive from the left to the right in FIG. 10.

A distance between positive discharge electrode 2 and negative discharge electrode 2 in one ion-generating element 10c was set to be E1. A distance between positive discharge electrode 2 in ion-generating element 10c located on the left in the drawing and negative discharge electrode 2 in ion-generating element 10c located on the right in the drawing was set to be P1.

Figure 11:
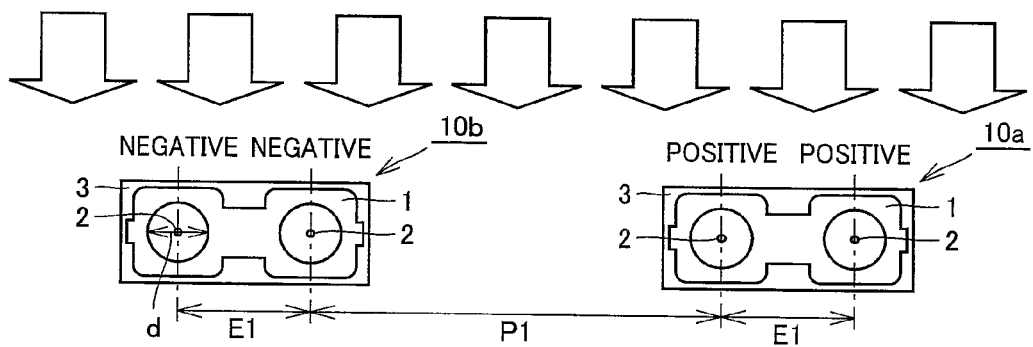
FIG. 11 is a schematic plan view that shows a configuration of two ion-generating elements having a polarity arrangement of negative/negative/positive/positive, which ion-generating elements are prepared for studying the relation between a diameter of a through hole of each of the induction electrodes and an optimal distance between the positive discharge electrode and the negative discharge electrode.

Furthermore, two ion-generating elements 10a, 10b as shown in FIG. 11 were also prepared. These two ion-generating elements 10a, 10b were the same as those shown in FIG. 10 in configuration and disposition, and the arrangement of polarity of discharge electrodes 2 was modified. In the two ion-generating elements 10a, 10b in FIG. 11, the arrangement of polarity of discharge electrodes 2 was in order of negative/negative/positive/positive from the left to the right in FIG. 11.

A distance between discharge electrodes 2 in each of ion-generating elements 10a, 10b, 10c was set to be E1. A distance between negative discharge electrode 2 in ion-generating element 10a located on the left in the drawing and positive discharge electrode 2 in ion-generating element 10b located on the right in the drawing was set to be P1.

As to both of FIGS. 10 and 11, air was blown under the same condition in a direction from the rear to the front of the ion-generating elements (in the direction of an arrow in the drawing), and an ion concentration at a prescribed downwind distance was measured. The results show that an amount of ions generated by the polarity arrangement of discharge electrodes 2 shown in FIG. 11 was increased 1.3 times as to positive ions, and increased 1.5 times as to negative ions, when compared with an amount of ions generated by the polarity arrangement of discharge electrodes 2 shown in FIG. 10. The above-described results show that the polarity arrangement of discharge electrodes 2 shown in FIG. 11 was more preferable than the polarity arrangement of discharge electrodes 2 shown in FIG. 10.

Further, by adopting a configuration in which common induction electrode 1 is provided for a plurality of discharge electrodes 2 for generating ions of the same polarity, namely, a positive polarity or a negative polarity, it was also possible to generate ions at a plurality of sites and increase an amount of generated ions.

In the above-described experiment, a diameter of through hole 1a of induction electrode 1 and a voltage to be applied were determined so as to cause corona discharge at the tip of each of discharge electrodes 2. The ratio (E1/d) of distance E1 with respect to diameter d of through hole 1a was 2, while the ratio (P1/d) of distance P1 with respect to diameter d of through hole 1a was 6.7.

Further studies were conducted on changes in ion concentration when distance P1 was changed in the polarity arrangement in FIG. 11. The results are shown in FIG. 12.

Figure 12:
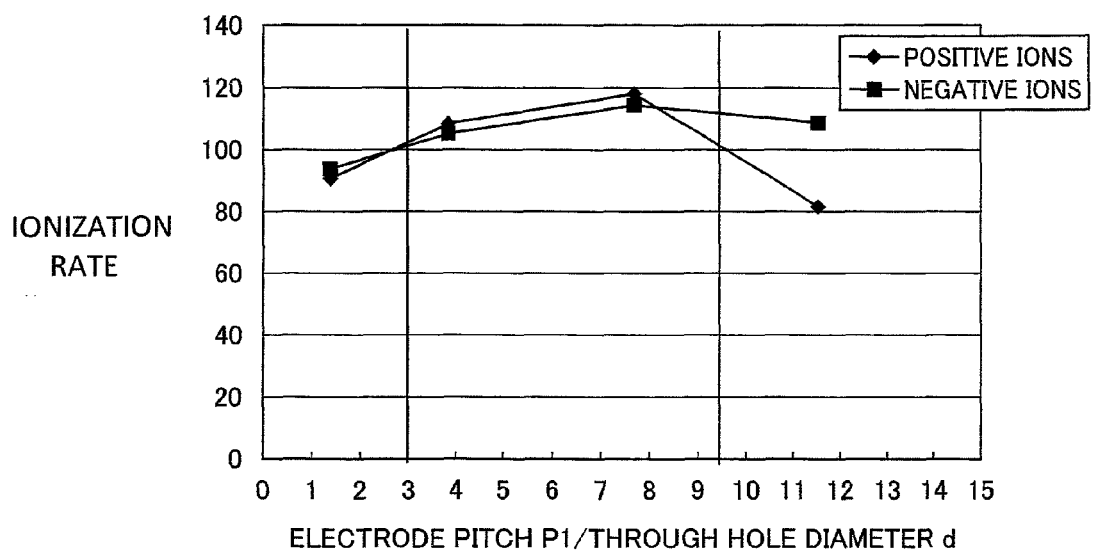
FIG. 12 is a diagram that shows the relation between a diameter of a through hole of the induction electrode and a distance between the positive discharge electrode and the negative discharge electrode.

Reference is made to FIG. 12. When distance P1 was changed, the following tendency was observed: until a value (P1/d), which is obtained by dividing distance P1 by a diameter value d of through hole 1a, reached approximately 7.5, both of positive ions and negative ions were increased, and when the value (P1/d) exceeded 7.5, both of positive ions and negative ions were decreased. It was also found that an ionization rate of 100 or more, which is a sufficient indicator of elimination of funguses and the like floating in the air, could be obtained when the ratio (P1/d) was 3 or more and 9.5 or less.

Figure 13:
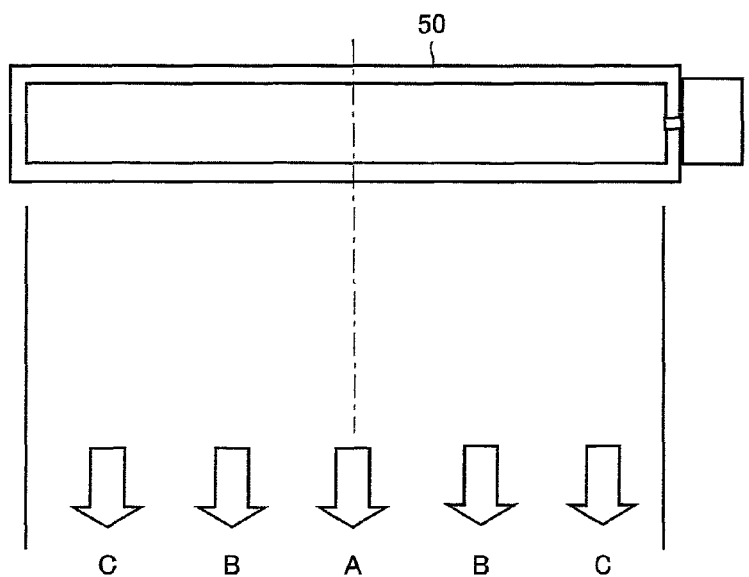
FIG. 13 is a drawing for describing that a wind speed differs among respective portions in a cross flow fan.

When ion-generating device 30 in the present embodiment is considered to be mounted on an electrical apparatus, cross flow fan 50 as shown in FIG. 13 and a sirocco fan as shown in FIGS. 8 and 9 are generally considered as a fan for the air-conditioning unit. In any of the fans, when the wind speed is measured, it varies depending on measurement sites. The wind speeds at measurement sites A, B, and C shown in FIGS. 13 and 9, respectively, were in the order of A>B>C, namely, the wind speed at the center of the fan became higher, while the wind speed at the end portions became lower.

When ion-generating device 30 is considered to be mounted on an electrical apparatus, excessively-large distance P1 causes increase in width of ion-generating device 30 itself, and general versatility is decreased because the air-blowing condition is deteriorated as described above. Excessively-large distance P1 is not appropriate, and in consideration of the dimension of the electrical apparatus on which ion-generating device 30 is to be mounted, it is appropriate to set a longitudinal width of the ion-generating device to be 150 mm or less.

If diameter d of through hole 1a of induction electrode 1 is increased, the distance between discharge electrode 2 and induction electrode 1 is increased, and thus the probability that ions generated from discharge electrode 2 are neutralized at induction electrode 1 is decreased, and neutralization of the ions can be reduced. However, excessively-large diameter d causes increase in required voltage to be applied, resulting in increased size of the circuit. Furthermore, increase in physical size of induction electrode 1 causes increase in size of entire ion-generating device 30. Accordingly, there is a limitation on increase in diameter d from a viewpoint of achieving reduced thickness and compactness.

In contrast, if diameter d is excessively small, the range between a discharge start voltage and a spark discharge transition voltage becomes small, which makes it difficult to set a voltage to be applied. Since a radius (d/2) of through hole 1a of induction electrode 1 can approximate to the distance between discharge electrode 2 and induction electrode 1, the relation of d<P1 is established between distance P1 and diameter d. Here, if distance P1 is small, the emitted positive ions and negative ions are more likely to be attracted by Coulomb force. In contrast, if distance P1 is excessively large, positive discharge electrode 2 and negative discharge electrode 2 become remote, and this arrangement is similar to that in the case of monopolar ion emission. The monopolar ion emission is not appropriate because it causes the surroundings to be electrically charged. Furthermore, when ion-generating device 30 is considered to be mounted on an electrical apparatus, a wind speed condition may be deteriorated. Therefore, excessively-large distance P1 is not appropriate as well. In view of the foregoing, the relation between diameter d of through hole 1a of induction electrode 1 and distance P1 between positive discharge electrode 2 and negative discharge electrode 2 is preferably d<P1<150 mm and $3 \leq P1/d \leq 9.5$.

Distance P1 corresponding to the above-described ratio (P1/d) is preferably 35-115 mm, and particularly preferably 96 mm. Diameter d corresponding to the above-described ratio (P1/d) is preferably $\phi 10$ mm-$\phi 15$ mm, and particularly preferably $\phi 12$ mm-$\phi 13$ mm.

In consideration of the optimal disposition of ion-generating elements 10a, 10b, and the like in casing 21 so as to achieve a thin and compact ion-generating device, it is important to separate positive ion-generating element 10a and negative ion-generating element 10b by an appropriate distance as described above. By doing so, a space is ensured between positive ion-generating element 10a and negative ion-generating element 10b. To achieve a reduced thickness, it is efficient to dispose high-voltage transformer 11 and high voltage-generating circuit 20 in this space. It is possible to achieve a reduced thickness by adopting a planar disposition in which the electrode/the circuit/the electrode are arranged in this order in plan view, and achieve compactness by effectively utilizing the above-described space.

(Second Embodiment)

Figure 14:
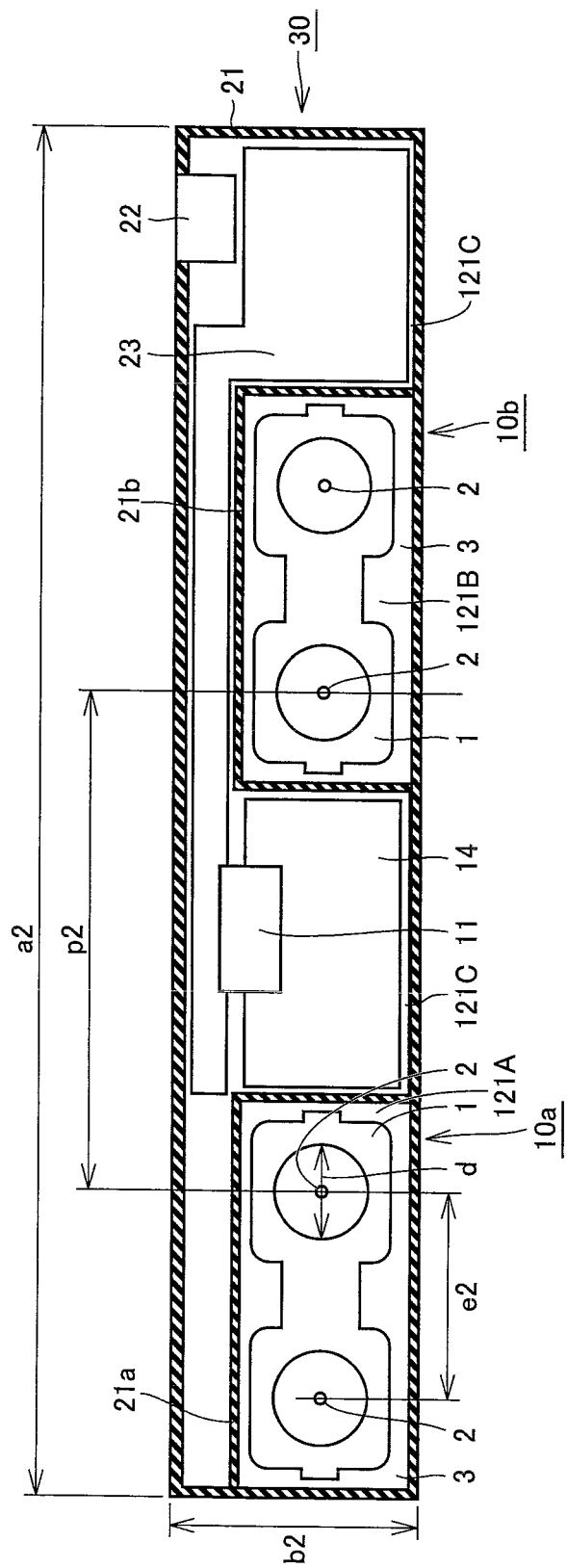
FIG. 14 is a schematic plan view of a configuration of an ion-generating device in a second embodiment of the present invention, when seen from a bottom surface side of a casing, and shows a bottom plate portion of the casing and a molding resin in perspective.

FIG. 14 is a schematic plan view of a configuration of an ion-generating device in a second embodiment of the present invention, when seen from a bottom surface side of a casing, and shows a bottom plate portion of the casing and a molding resin in perspective. With reference to FIG. 14, the configuration of the present embodiment differs from the configuration of the first embodiment in the positions at which high-voltage transformer 11, high-voltage circuits 12a, 12b, power supply circuit 23, and power supply input connector 22 are disposed.

In the present embodiment, the entire substrate 14 supporting high-voltage circuits 12a, 12b is disposed in a space between region 121A for disposing the positive ion-generating element and region 121B for disposing the negative ion-generating element.

Both of power supply input connector 22 and at least a part of the region for disposing power supply circuit 23 are located on a side opposite to region 121A for disposing the positive ion-generating element with respect to region 121B for disposing the negative ion-generating element. It is noted that both of power supply input connector 22 and at least a part of the region for disposing power supply circuit 23 may be located on a side opposite to region 121B for disposing the negative ion-generating element with respect to region 121A for disposing the positive ion-generating element. In other words, power supply input connector 22 and power supply circuit 23 are disposed on an outside of any one of region 121B for disposing the negative ion-generating element and region 121A for disposing the positive ion-generating element.

By doing so, in the planar layout of the present embodiment, the ion-generating element unit/the circuit unit/the ion-generating element unit/the circuit unit are arranged in this order from the left to the right in FIG. 14, so that the connector is disposed at the outermost position.

A distance e2 between positive discharge electrodes 2 and a distance p2 between positive discharge electrode 2 and negative discharge electrode 2 are approximately equal to dimension e1 and dimension p1 shown in FIG. 1, respectively, from the results of experiments shown in FIGS. 10 and 11.

An external shape of outer casing 21 is defined by a length a1×a width b1×a thickness c1 (not shown, see FIG. 2), and is preferably a thin and compact shape having a1 of 70-150 mm, b1 of 20-40 mm, and c1 of 8-10 mm.

It is noted that other configurations of the present embodiment are almost the same as the configurations of the first embodiment described above, and hence the same elements are provided with the same reference characters, and the description thereof will not be repeated.

Next, description will be made on functional effects of the present embodiment.

Power supply input connector 22, which receives input power supply, is preferably disposed at the center of casing 21 as shown in FIG. 1, so as not to allow a wiring to power supply input connector 22 to disturb the air blown to the electrode units.

In some cases, however, power supply input connector 22 located at a site other than the above-described center may improve wiring efficiency to power supply input connector 22. In that case, however, it is necessary to be careful not to allow the wiring to power supply input connector 22 to block the air blown to electrodes 1, 2.

Therefore in the present embodiment, high voltage-generating circuit 20 is disposed in a space between positive ion-generating element 10a and negative ion-generating element 10b, and power supply circuit 23 and power supply input connector 22 are disposed on an outside of ion-generating element 10a or 10b. It is thereby possible to dispose the respective configuration members in a planar manner in the arrangement of the electrode/the circuit/the electrode/the circuit in casing 21, so that it is possible to achieve a reduced thickness and dispose power supply input connector 22 separately from ion-generating elements 10a, 10b. The lead for connecting to the power supply input connector is thereby prevented from disturbing the air blown in the vicinity of the ion-generating elements.

It is noted that positive induction electrode 1 and negative induction electrode 1, which are structurally separated from each other, are preferably electrically connected such that positive discharge electrode 2 is at a potential positive with respect to positive induction electrode 1, and that negative discharge electrode 2 is at a potential negative with respect to negative induction electrode 1.

Figure 15:
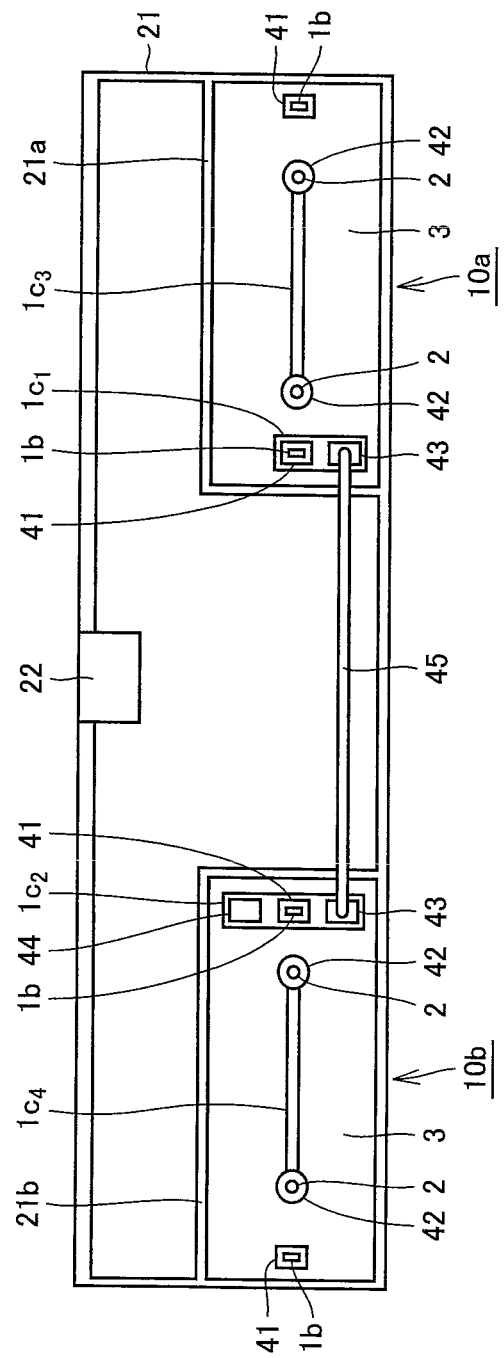
FIG. 15 is a schematic plan view that shows how a positive induction electrode and a negative induction electrode are electrically connected, when seen from a lid side of the casing of the ion-generating device, and shows a lid of the casing and a molding resin in perspective.

FIG. 15 is a schematic plan view that shows how each of the positive and negative induction electrodes are electrically connected, when seen from a lid side of the casing of the ion-generating device, and shows the lid of the casing and a molding resin in perspective. In FIG. 15, illustration of the circuit unit is eliminated.

With reference to FIG. 15, positive induction electrode 1 and negative induction electrode 1 are preferably electrically connected to each other via, for example, a jumper wire (induction electrode connecting wire) 45. Opposite end portions of jumper wire 45 are electrically connected to induction electrodes 1 via jumper wire solder pads 43, wiring patterns $1c_1$, $1c_2$, and induction electrode solder pads 41, respectively.

One end portion of jumper wire 45 is electrically connected to jumper wire solder pad 43 in ion-generating element 10a by solder (not shown). Jumper wire solder pad 43 in ion-generating element 10a is electrically connected to induction electrode solder pad 41 via wiring pattern $1c_1$. Induction electrode solder pad 41 is electrically connected to bent portion 1b of induction electrode 1 by solder (not shown).

The other end portion of jumper wire 45 is electrically connected to jumper wire solder pad 43 in ion-generating element 10b by solder (not shown). Jumper wire solder pad 43 in ion-generating element 10b is electrically connected to induction electrode solder pad 41 and another solder pad 44 via wiring pattern $1c_2$. Induction electrode solder pad 41 is electrically connected to bent portion 1b of induction electrode 1 by solder (not shown). Other solder pad 44 is electrically connected to a terminal of the high-voltage transformer, for example, by solder (not shown).

It is necessary for jumper wire 45 to extend over first partition 21a and second partition 21b, so that jumper wire 45 is disposed by being lifted slightly off of a solder-bonding plane of substrate 3, except for a portion connected to jumper wire solder pad 43.

It is noted that each discharge electrode 2 is electrically connected to a discharge electrode solder pad 42 by solder (not shown). Discharge electrode solder pads 42 in ion-generating element 10a are electrically connected to each other via a wiring pattern $1c_3$, and discharge electrode solder pads 42 in ion-generating element 10b are electrically connected to each other via a wiring pattern $1c_4$. Thereby, positive discharge electrodes 2 are electrically connected to each other, and negative discharge electrodes 2 are electrically connected to each other.

It is noted that, although FIG. 15 shows the configuration applied to the configuration of the above-described first embodiment, it is clear that the configuration is similarly applicable to the configuration of the above-described second embodiment.

It should be understood that the embodiments disclosed herein are illustrative and not limitative in all aspects. The scope of the present invention is shown not by the description above but by the scope of the claims, and is intended to include all modifications within the equivalent meaning and scope of the claims.

Industrial Applicability

The present invention can be applied particularly advantageously to an ion-generating device in which a positive ion-generating unit and a negative ion-generating unit are disposed in a casing, and an electrical apparatus provided with the ion-generating device.

Description of the Reference Signs

1: induction electrode, 1a: through hole, 1b: bent portion, 1c: wiring portion, $1c_1$, $1c_2$, $1c_3$, $1c_4$: wiring pattern, 2: discharge electrode, 3: supporting substrate, 3a, 3b: through hole, 10a, 10b, 10c: ion-generating element, 11: high-voltage transformer, 12a, 12b: high-voltage circuit, 14: substrate, 20: high voltage-generating circuit, 21: outer casing, 21a, 21b: partition, 21c: step, 21d, 25a: ion-emission hole, 22: power supply input connector, 23: power supply circuit, 24: lid, 25: electrode lid, 30: ion-generating device, 31: molding resin, 41: induction electrode solder pad, 42: discharge electrode solder pad, 43: jumper wire solder pad, 44: solder pad, 45: jumper wire, 50: cross flow fan, 60: air-cleaning unit, 61: front panel, 62: body, 63: outlet port, 64: air intake port, 65: fan casing, 121A: region for disposing positive ion-generating element, 121B: region for disposing negative ion-generating element, 121C: region for disposing high voltage-generating circuit and the like.

The invention claimed is:

1. An ion-generating device, comprising:
   a positive ion-generating unit including a positive discharge electrode, and a first induction electrode for generating positive ions between said first induction electrode and said positive discharge electrode;
   a negative ion-generating unit including a negative discharge electrode, and a second induction electrode for generating negative ions between said second induction electrode and said negative discharge electrode, wherein
   said positive ion-generating unit and said negative ion-generating unit being disposed with a space interposed therebetween, such that said first induction electrode and said second induction electrode are separated from each other; and
   a circuit unit having a portion disposed in said space between said positive ion-generating unit and said negative ion-generating unit.

2. The ion-generating device according to claim 1, further comprising
   a first substrate holding both of said positive discharge electrode and said first induction electrode, and
   a second substrate holding both of said negative discharge electrode and said second induction electrode, wherein
   said positive ion-generating unit and said negative ion-generating unit are disposed with said space interposed therebetween, such that said first substrate and said second substrate are separated from each other.

3. The ion-generating device according to claim 1, wherein
   said circuit unit includes a high voltage-generating circuit for applying a voltage to each of said positive ion-generating unit and said negative ion-generating unit, and
   at least a part of said high voltage-generating circuit is disposed in said space between said positive ion-generating unit and said negative ion-generating unit.

4. The ion-generating device according to claim 1, further comprising a casing in which said positive ion-generating unit, said negative ion-generating unit, and said circuit unit are disposed, wherein
   said casing has a first partition for isolating a region for disposing said positive ion-generating unit from a region for disposing said circuit unit, and a second partition for isolating a region for disposing said negative ion-generating unit from each of the region for disposing said positive ion-generating unit and the region for disposing said circuit unit.

5. The ion-generating device according to claim 1, wherein
   said circuit unit includes a power supply circuit for providing an input voltage to said high voltage-generating circuit and driving said high voltage-generating circuit,
   the ion-generating device further comprises a power supply input connector electrically connected to said power supply circuit, and
   said power supply input connector and at least a part of a region for disposing said power supply circuit in said casing are located on any of a side opposite to said space with respect to said positive ion-generating unit and a side opposite to said space with respect to said negative ion-generating unit.

6. The ion-generating device according to claim 1, wherein a spacing between said positive discharge electrode and said negative discharge electrode is 35 mm or more and 115 mm or less.

7. The ion-generating device according to claim 1, wherein
   said first induction electrode has a first through hole at a position facing a tip of said positive discharge electrode,
   said second induction electrode has a second through hole at a position facing a tip of said negative discharge electrode, and
   a ratio of a spacing between said positive discharge electrode and said negative discharge electrode with respect to each of a diameter of said first through hole and a diameter of said second through hole is 3 or more and 9.5 or less.

8. An electrical apparatus, comprising:
   the ion-generating device recited in claim 1; and
   an air blow unit for delivering both of the positive ions and the negative ions generated at said ion-generating device on a blown air stream to an outside of the electrical apparatus.

9. An ion-generating device, comprising:
   a positive ion-generating unit including a positive discharge electrode, and a first induction electrode for generating positive ions between said first induction electrode and said positive discharge electrode;
   a negative ion-generating unit including a negative discharge electrode, and a second induction electrode for generating negative ions between said second induction electrode and said negative discharge electrode, wherein
   said positive ion-generating unit and said negative ion-generating unit being disposed with a space interposed therebetween, by allowing said first induction electrode and said second induction electrode to be spaced apart; and a circuit unit having a portion disposed in said space between said positive ion-generating unit and said negative ion-generating unit.

10. The ion-generating device according to claim 9, further comprising
a first substrate holding both of said positive discharge electrode and said first induction electrode, and
a second substrate holding both of said negative discharge electrode and said second induction electrode, wherein
said positive ion-generating unit and said negative ion-generating unit are disposed with said space interposed therebetween, such that said first substrate and said second substrate are separated from each other.

11. The ion-generating device according to claim 9, wherein
said circuit unit includes a high voltage-generating circuit for applying a voltage to each of said positive ion-generating unit and said negative ion-generating unit, and
at least a part of said high voltage-generating circuit is disposed in said space between said positive ion-generating unit and said negative ion-generating unit.

12. The ion-generating device according to claim 9, further comprising a casing in which said positive ion-generating unit, said negative ion-generating unit, and said circuit unit are disposed, wherein
said casing has a first partition for isolating a region for disposing said positive ion-generating unit from a region for disposing said circuit unit, and a second partition for isolating a region for disposing said negative ion-generating unit from each of the region for disposing said positive ion-generating unit and the region for disposing said circuit unit.

13. The ion-generating device according to claim 9, wherein
said circuit unit includes a power supply circuit for providing an input voltage to said high voltage-generating circuit and driving said high voltage-generating circuit,
the ion-generating device further comprises a power supply input connector electrically connected to said power supply circuit, and
said power supply input connector and at least a part of a region for disposing said power supply circuit in said casing are located on any of a side opposite to said space with respect to said positive ion-generating unit and a side opposite to said space with respect to said negative ion-generating unit.

14. The ion-generating device according to claim 9, wherein a spacing between said positive discharge electrode and said negative discharge electrode is 35 mm or more and 115 mm or less.

15. The ion-generating device according to claim 9, wherein
said first induction electrode has a first through hole at a position facing a tip of said positive discharge electrode,
said second induction electrode has a second through hole at a position facing a tip of said negative discharge electrode, and
a ratio of a spacing between said positive discharge electrode and said negative discharge electrode with respect to each of a diameter of said first through hole and a diameter of said second through hole is 3 or more and 9.5 or less.

16. An electrical apparatus, comprising:
the ion-generating device recited in claim 9; and
an air blow unit for delivering both of the positive ions and the negative ions generated at said ion-generating device on a blown air stream to an outside of the electrical apparatus.

17. An ion-generating device, comprising:
a positive ion-generating unit for generating positive ions, including a first induction electrode disposed such that a positive discharge electrode is dischargeable;
a negative ion-generating unit for generating negative ions, including a second induction electrode disposed such that a negative discharge electrode is dischargeable; in a body, wherein
said positive ion-generating unit and said negative ion-generating unit being disposed with a space interposed therebetween, the space being for preventing the generated positive ions and the generated negative ions from being neutralized by each other; and
a circuit unit having a portion disposed in said space between said positive ion-generating unit and said negative ion-generating unit.

18. The ion-generating device according to claim 17, further comprising
a first substrate holding both of said positive discharge electrode and said first induction electrode, and
a second substrate holding both of said negative discharge electrode and said second induction electrode, wherein
said positive ion-generating unit and said negative ion-generating unit are disposed with said space interposed therebetween, such that said first substrate and said second substrate are separated from each other.

19. The ion-generating device according to claim 17, wherein
said circuit unit includes a high voltage-generating circuit for applying a voltage to each of said positive ion-generating unit and said negative ion-generating unit, and
at least a part of said high voltage-generating circuit is disposed in said space between said positive ion-generating unit and said negative ion-generating unit.

20. The ion-generating device according to claim 17, further comprising a casing in which said positive ion-generating unit, said negative ion-generating unit, and said circuit unit are disposed, wherein
said casing has a first partition for isolating a region for disposing said positive ion-generating unit from a region for disposing said circuit unit, and a second partition for isolating a region for disposing said negative ion-generating unit from each of the region for disposing said positive ion-generating unit and the region for disposing said circuit unit.

21. The ion-generating device according to claim 17, wherein
said circuit unit includes a power supply circuit for providing an input voltage to said high voltage-generating circuit and driving said high voltage-generating circuit,
the ion-generating device further comprises a power supply input connector electrically connected to said power supply circuit, and
said power supply input connector and at least a part of a region for disposing said power supply circuit in said casing are located on any of a side opposite to said space with respect to said positive ion-generating unit and a side opposite to said space with respect to said negative ion-generating unit.

22. The ion-generating device according to claim 17, wherein a spacing between said positive discharge electrode and said negative discharge electrode is 35 mm or more and 115 mm or less.

23. The ion-generating device according to claim 17, wherein
said first induction electrode has a first through hole at a position facing a tip of said positive discharge electrode,
said second induction electrode has a second through hole at a position facing a tip of said negative discharge electrode, and
a ratio of a spacing between said positive discharge electrode and said negative discharge electrode with respect to each of a diameter of said first through hole and a diameter of said second through hole is 3 or more and 9.5 or less.

24. An electrical apparatus, comprising:
the ion-generating device recited in claim 17; and
an air blow unit for delivering both of the positive ions and the negative ions generated at said ion-generating device on a blown air stream to an outside of the electrical apparatus.

25. An ion-generating device, comprising:
a positive ion-generating unit for generating positive ions, the positive ion-generating unit being disposed such that a positive discharge electrode is dischargeable;
a negative ion-generating unit for generating negative ions, the negative ion-generating unit being disposed such that a negative discharge electrode is dischargeable; in a body, wherein
said positive ion-generating unit and said negative ion-generating unit being disposed with a space interposed therebetween, the space being for preventing the generated positive ions and the generated negative ions from being neutralized by each other; and
a circuit unit having a portion disposed in said space between said positive ion-generating unit and said negative ion-generating unit.

26. The ion-generating device according to claim 25, wherein
said circuit unit includes a high voltage-generating circuit for applying a voltage to each of said positive ion-generating unit and said negative ion-generating unit, and
at least a part of said high voltage-generating circuit is disposed in said space between said positive ion-generating unit and said negative ion-generating unit.

27. The ion-generating device according to claim 25, further comprising a casing in which said positive ion-generating unit, said negative ion-generating unit, and said circuit unit are disposed, wherein
said casing has a first partition for isolating a region for disposing said positive ion-generating unit from a region for disposing said circuit unit, and a second partition for isolating a region for disposing said negative ion-generating unit from each of the region for disposing said positive ion-generating unit and the region for disposing said circuit unit.

28. The ion-generating device according to claim 25, wherein
said circuit unit includes a power supply circuit for providing an input voltage to said high voltage-generating circuit and driving said high voltage-generating circuit,
the ion-generating device further comprises a power supply input connector electrically connected to said power supply circuit, and
said power supply input connector and at least a part of a region for disposing said power supply circuit in said casing are located on any of a side opposite to said space with respect to said positive ion-generating unit and a side opposite to said space with respect to said negative ion-generating unit.

29. The ion-generating device according to claim 25, wherein a spacing between said positive discharge electrode and said negative discharge electrode is 35 mm or more and 115 mm or less.

30. An electrical apparatus, comprising:
the ion-generating device recited in claim 25; and
an air blow unit for delivering both of the positive ions and the negative ions generated at said ion-generating device on a blown air stream to an outside of the electrical apparatus.

* * * * *